(12) United States Patent
Brotherson

(10) Patent No.: US 8,759,050 B2
(45) Date of Patent: *Jun. 24, 2014

(54) PROCESS AND SYSTEM FOR PRODUCING ETHANOL FROM A BYPRODUCT OF AN ETHANOL PRODUCTION FACILITY

(75) Inventor: Travis Brotherson, Holstein, IA (US)

(73) Assignee: Quad County Corn Processors, Galva, IA (US)

( * ) Notice: Subject to any disclaimer, the term of this patent is extended or adjusted under 35 U.S.C. 154(b) by 205 days.

This patent is subject to a terminal disclaimer.

(21) Appl. No.: 13/238,969

(22) Filed: Sep. 21, 2011

(65) Prior Publication Data

US 2012/0244591 A1 Sep. 27, 2012

Related U.S. Application Data

(63) Continuation-in-part of application No. 13/026,613, filed on Feb. 14, 2011.

(51) Int. Cl.
*C12P 7/10* (2006.01)
*C12P 7/14* (2006.01)

(52) U.S. Cl.
USPC .......................................... 435/161; 435/164

(58) Field of Classification Search
USPC ....................................................... 435/164
See application file for complete search history.

(56) References Cited

U.S. PATENT DOCUMENTS

| | | | |
|---|---|---|---|
| 3,990,945 | A | 11/1976 | Huff et al. |
| 6,660,506 | B2 | 12/2003 | Nguyen et al. |
| 7,527,941 | B1 | 5/2009 | Hogen et al. |
| 2004/0023349 | A1 | 2/2004 | Bisgaard-Frantzen et al. |
| 2010/0159552 | A1 | 6/2010 | Benson et al. |
| 2010/0196979 | A1 | 8/2010 | Birkmire et al. |
| 2012/0208252 | A1* | 8/2012 | Brotherson .................. 435/165 |

OTHER PUBLICATIONS

Production of Acetone-Butanol-Ethanol (ABE) using distillers dried grains with solubles (DDGS): Pentose sugar utilization and impact of degradation products; Midwest Consortium for Biobased Products & Bioenergy; University of Illinois; Dr. Hans Blaschek, Dr. Thaddeus Ezeji; printed Feb. 14, 2011.

Research Challenges and Opportunities for Cellulose Conversion Technology in a Dry Mill Pathway; Midwest Consortium for Biobased Products & Bioenergy; Michael Ladisch, Nathan Mosier, Wally Tyner, Nancy Ho. Mira Sedlak; Lorre, Purdue University; Mike Cotta, Bruce Dien, Xin-Liang Li, Eduardo Ximenes, USDA NCAUR, Hans Blaschek, Thaddeus Ezeji, University of Illinois, Bruce Dale, Dalan Venkatesh, Michigan State University, Brent Shaks, Iowa State University, John Verkade, Ames Laboratory, Gene Petersen, Golden Field Office DOE; printed Feb. 14, 2011.

Applied Biochemistry and Biotechnology; vols. 113-116 (12 Issues). Spring 2004, ISSN: 0273-2289; Biotechnology for Fuels and Chemicals The Twenty-Fifth Symposium; Mark Kinkelstein, James D. McMillan, Brian H. Davison, Barbara Evans.

Cellulose conversion in dry grind ethanol plants; Science Direct, Bioresource Technology 99 (2008) 5157-5159; Michael Ladisch, Bruce Dale, Wally Tyner, Nathan Mosier, Youngmi Kim, Michael Cotta, Bruce Dien, Hans Blaschek, Edmund Laurenas, Brent Shanks, John Verkade, Chad Schell, Gene Petersen; Copyright 2007 Published by Elsevier Ltd.

* cited by examiner

*Primary Examiner* — Tekchand Saidha
(74) *Attorney, Agent, or Firm* — Myers Bigel Sibley & Sajovec

(57) ABSTRACT

A process of producing ethanol from whole stillage, includes obtaining a supply of whole stillage from an ethanol production facility after ethanol has been extracted therefrom; pre-treating the whole stillage to convert hemicellulose portions of the whole stillage into sugars; adding enzymes to the whole stillage to convert cellulose portions of the whole stillage to sugars; fermenting the whole stillage to create a beer mixture; and distilling the beer mixture to separate ethanol therefrom. The pre-treating step may include adding acid to the whole stillage to decrease its pH level; heating and pressurizing the whole stillage; holding the whole stillage under pressure and heat for a dwell time; removing pressure from the whole stillage to cause flashing; and cooling the whole stillage before the enzymes are added.

10 Claims, 4 Drawing Sheets

PROCESS AND SYSTEM FOR PRODUCING ETHANOL FROM A BYPRODUCT OF AN ETHANOL PRODUCTION FACILITY

RELATED APPLICATIONS

This application is a continuation in part of identically titled application Ser. No. 13/026,613, filed Feb. 14, 2011, incorporated by reference herein in its entirety.

BACKGROUND

The present invention relates to ethanol production processes and systems. More particularly, the invention relates to processes and systems for producing additional ethanol from byproducts of an ethanol production facility.

The production of ethanol for use as a gasoline additive or a straight liquid fuel continues to increase as petroleum costs rise and environmental concerns become more pronounced. Ethanol may be produced in a dry milling process by grinding corn or other grains into a powder or flour and then liquefying, fermenting, and distilling it to produce alcohol, carbon dioxide, and byproducts. Conventional ethanol production processes produce ethanol from the starch portion of the grain but do not produce any usable ethanol from the fiber portions of the grain, which are primarily found in the byproducts. Instead, the byproducts are typically dehydrated and used as animal feed. Moreover, because the byproducts are high in fiber content, the resultant animal feed is difficult for monogastrics to digest.

SUMMARY

The present invention solves the above-described problems and provides a distinct advance in the art of ethanol production processes. More particularly, the present invention provides processes and systems for producing additional ethanol from whole stillage (also commonly referred to as "distiller's grains" or "spent distiller's grains") or other byproducts of an ethanol production facility. The processes and systems of the present invention also improve the nutritional content and value of the animal feed produced from the byproducts of the process.

An embodiment of the invention is a process of producing additional ethanol from whole stillage that comprises obtaining a supply of whole stillage from an ethanol production facility after ethanol has been extracted therefrom; pre-treating the whole stillage to convert hemicellulose portions of the whole stillage into sugars; adding enzymes to the whole stillage to convert cellulose portions of the whole stillage to sugars; fermenting the whole stillage to create a beer mixture; and distilling the beer mixture to separate ethanol therefrom.

The pre-treating steps may comprise adding acid to the whole stillage to decrease its pH level; heating and pressurizing the whole stillage; holding the whole stillage under pressure and heat for a dwell time; removing pressure from the whole stillage to cause flashing; and cooling the whole stillage before the enzymes are added.

The process may further comprise removing the whole stillage byproducts of the distilling step, separating the solids from the whole stillage, and drying the solids to form dried distillers grains.

The processes of the present invention advantageously produce additional ethanol from the byproducts of an ethanol production facility rather than just using the byproducts as animal feed. The processes of the present invention also result in a final byproduct that is higher in protein and lower in fiber and thus easier for monogastrics to digest.

This summary is provided to introduce a selection of concepts in a simplified form that are further described in the detailed description below. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
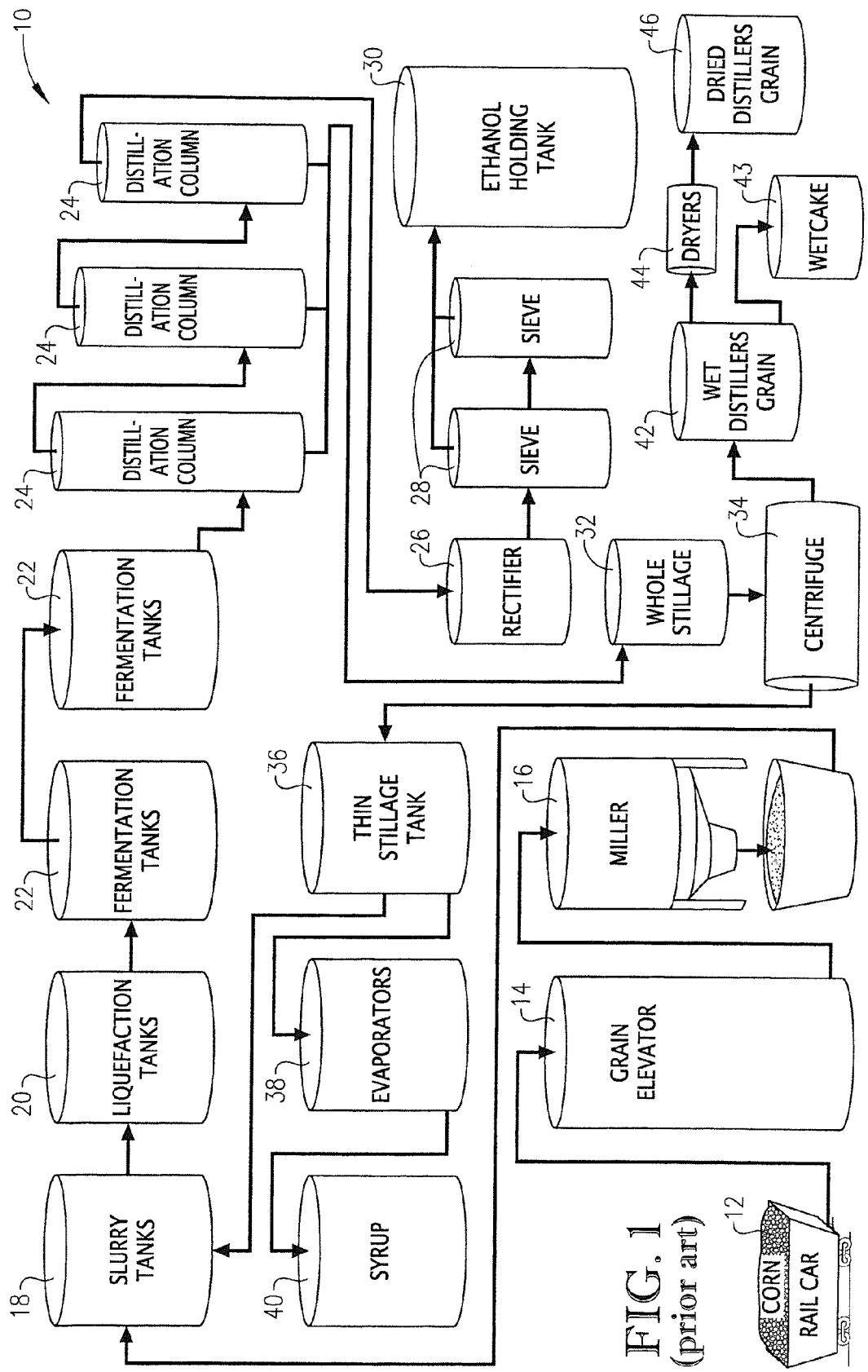
FIG. 1 is a schematic diagram of a prior art ethanol production facility.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings. The embodiments are intended to describe aspects of the invention in sufficient detail to enable those skilled in the art to practice the invention. Other embodiments can be utilized and changes can be made without departing from the scope of the claims. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

FIG. 1 is a schematic illustration of the primary components of a conventional ethanol production facility 10. The facility 10 is shown for purposes of describing aspects of the present invention and can be replaced, in whole or part, by other ethanol production facilities or components without departing from the scope of the present invention. Other ethanol production facilities and processes are described and illustrated in U.S. Pat. Nos. 6,660,506 and 7,527,941 and U.S.

Patent Application No. 2004/0023349, all of which are incorporated in their entireties into the present application by reference.

Returning to FIG. 1, grain 12 such as corn is first delivered to the ethanol production facility 10 by railcars, trucks, or other means. The grain may also be barley, rye, wheat, oats, sorghum, milo, canola, or soybeans. A sufficient supply of the grain to operate the production facility may be stored in one or more grain elevators 14, bins, or other storage vessels.

Ethanol production begins by milling or otherwise processing the grain into a fine powder or flour by a hammer mill or other milling machine 16. The milled grain is then mixed with water and enzymes in one or more slurry tanks 18 and held in these tanks or liquefaction tanks 20 for a sufficient amount of time to enable the enzymes to begin to breakdown the starch in the mixture into fermentable sugars.

The mixture is then passed to one or more fermentation tanks 22 where yeast is added. The fermenting process creates a mixture that contains alcohol, solids, and liquids and that is commonly referred to as "beer."

The beer is then transferred to one or more distillation columns 24, also often referred to as "beer strippers", which separate the alcohol from the solids and the liquids. The alcohol exits the top of these columns 24 and is transferred to one or more rectifiers 26 to remove moisture from the alcohol. The alcohol may also be passed to one or more molecular sieves 28 to remove even more moisture. The final alcohol is then transferred to one or more ethanol holding tanks 30 where it may be denatured before use as a fuel or fuel additive.

The liquid and solid mixture that remains in the distillation columns 24 after the alcohol has been removed is commonly referred to as "whole stillage" or simply "stillage". The mixture is also commonly referred to as "distiller's grains" or "spent distiller's grains." The whole stillage falls to the bottom of the distillation columns 24 and is then transferred to one or more whole stillage holding tanks 32. The whole stillage may then be passed through one or more centrifuges 34 which separate it into a stream of "thin stillage" and a stream of "wet distillers grain". The thin stillage is mostly liquid but may also contain a small amount of solid materials. The thin stillage may be held in one or more tanks and is typically returned to the slurry tanks 18 or some other part of the ethanol production facility 10 that requires water. Some or all of the thin stillage may also be transferred to one or more evaporators 38 to produce evaporated thin stillage, which is commonly referred to as "syrup". The syrup may be held in one or more tanks 40 and be used as an animal feed additive.

The wet distillers grain, which is often referred to as "wetcake", may be held in storage facilities 42, 43 and sold as a livestock feed. Some of the wet distillers grain may also be transferred to one or more dryers 44 to remove liquid therefrom to produce dried distillers grain, which may also be stored in one or more tanks 46 and used as livestock feed. In addition, some of the syrup can be dried with the wet distillers grains to produce dried distillers grains with solubles (DDGS).

The above described ethanol production facility 10 does not attempt to produce ethanol from the whole stillage removed from the distillation columns 24. Instead, the whole stillage is just a byproduct of the ethanol production process and is either used as livestock feed, make-up water, and/or is discarded. The processes of the present invention produce additional useable ethanol from the fiber portions of the whole stillage and any leftover starch after the main ethanol extraction is complete. The processes of the present invention also increase the protein content of the final byproducts, thus improving their nutrient value when used as livestock feed.

Since whole stillage is the byproduct of the fermentation of corn or other cereal grain, it contains a sizable fraction of fiber. All fiber is made up of hemicellulose, cellulose, and lignin Cellulose consists of glucose molecules, the same as in starch, but the linkages in cellulose make it more difficult to break down into individual glucose molecules than in starch. Hemicellulose contains a mixture of sugars and is generally easier to breakdown than cellulose. Lignin is a binder. The processes of the present invention include steps for converting both the hemicellulose and cellulose portions of the whole stillage into sugars that may be fermented into ethanol.

Figure 2:
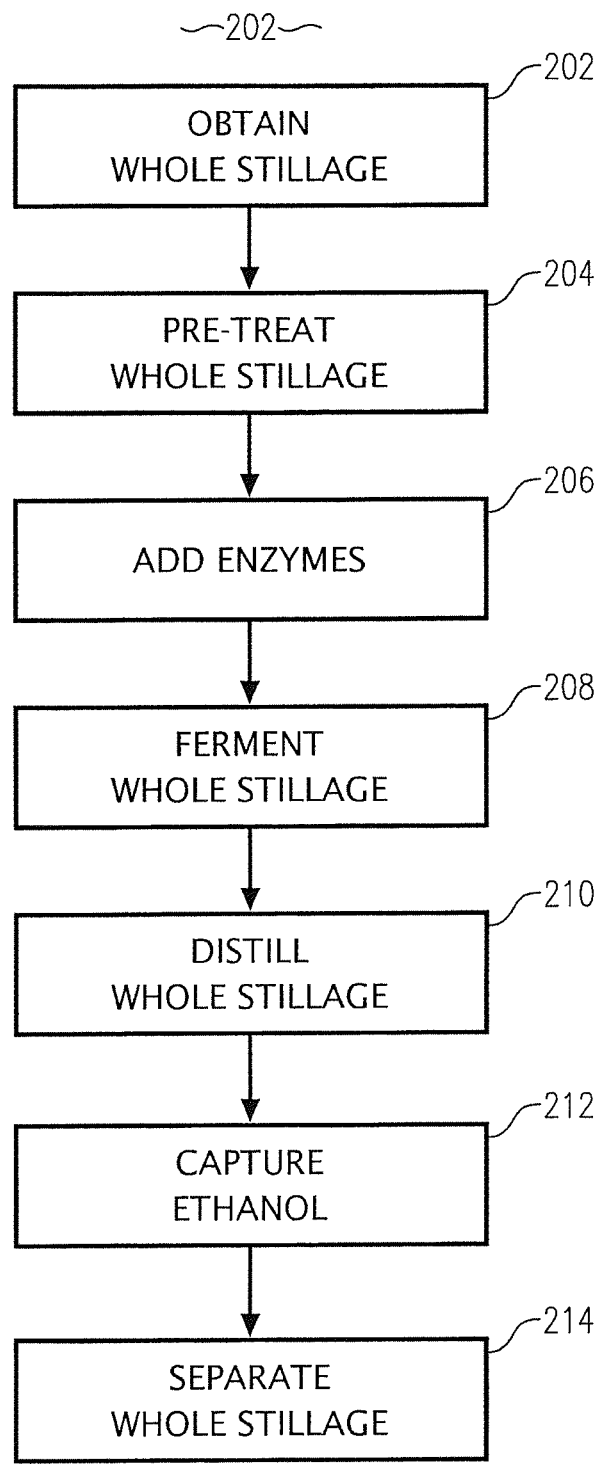
FIG. 2 is a flow diagram depicting a process of producing additional ethanol from byproducts of the ethanol production facility of FIG. 1.

The flow chart of FIG. 2 shows the steps in a process 200 for producing ethanol from whole stillage in accordance with embodiments of the invention. The functions noted in the various blocks may occur out of the order depicted in FIG. 2. For example, two blocks shown in succession in FIG. 2 may in fact be performed substantially concurrently, or the blocks may sometimes be performed in the reverse order depending upon the functionality involved.

Figure 3:
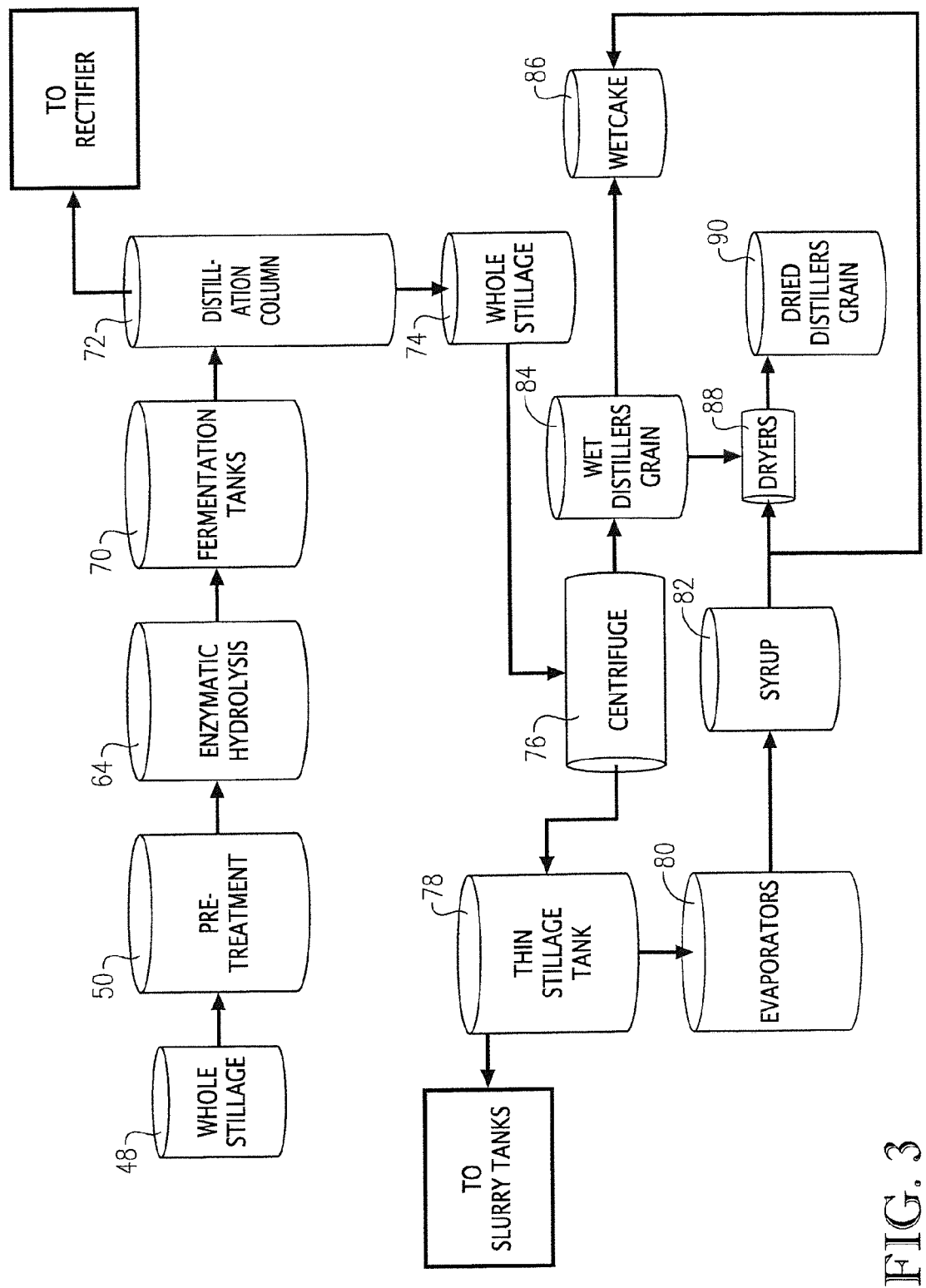
FIG. 3 is a schematic diagram of a system that may be used to implement the process of FIG. 2.
Figure 4:
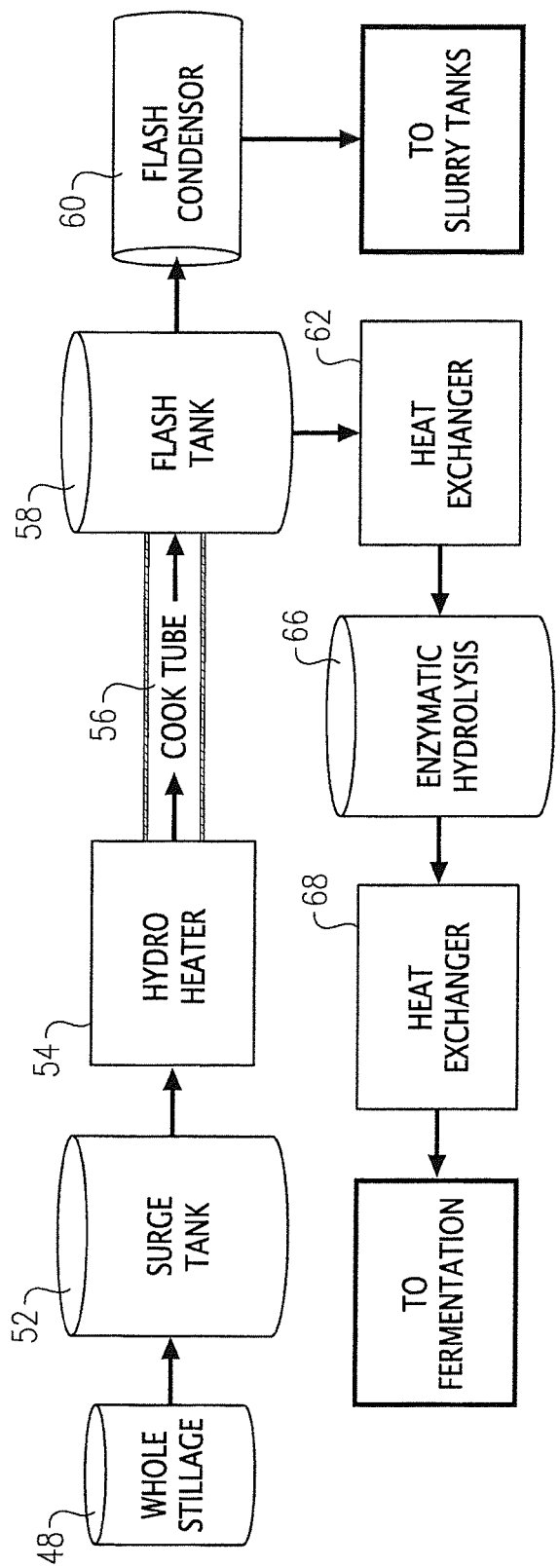
FIG. 4 is a schematic diagram depicting parts of the system of FIG. 3 in more detail.

Moreover, other embodiments of the process 200 may include additional steps not shown in FIG. 2 and/or may omit some of the steps shown in FIG. 2. The schematic diagrams of FIGS. 3 and 4 depict equipment that may be used to implement the process 200 and other embodiments of the process. The illustrated equipment may be replaced with other equipment without departing from the scope of the invention.

The process 200 starts by obtaining whole stillage as depicted in block 202. The whole stillage may be obtained from the distillation columns 24 or the whole stillage tanks 32 shown in FIG. 1 or elsewhere in the ethanol production facility 10 and may be held in one or more tanks 48 as depicted in FIG. 3. At this point in the process, the whole stillage has already been subjected to: 1) a long soak time in the liquefaction tanks 20 and fermenting tanks 22, 2) heating in the distillation steps, and 3) chemical reactions from the chemicals added throughout the ethanol production process. These steps help to facilitate the breakdown of the fiber in the whole stillage. The whole stillage is further treated in the process 200 of the present invention to continue the breakdown of the fiber for extracting additional ethanol.

The hydrolysis of fiber in the pretreatment method is determined by upstream plant processing and the severity of the pretreatment, as discussed in more detail below. The optimum settings for the parameters are then determined to target the most cost effective pretreatment and enzymatic hydrolysis. The hydrolysis rates and degree of depolymerization for cellulose and hemicellulose vary greatly between the pretreatment and enzymatic hydrolysis steps. In general, the cellulose has a greater tendency to depolymerize to the point of being very susceptible to hydrolyzation during the enzymatic treatment. Hemicellulose tends to become hydrolyzed to monomeric sugars during the pretreatment, but, depending on the enzymes used, can be somewhat difficult to hydrolyze completely by enzymes. For this reason, the required severity of the pretreatment is generally first determined by the desire for hemicellulose hydrolyzation.

If little to no hemicellulose hydrolyzation is required, the severity of the pretreatment is determined by the yield of glucose from cellulose during the enzymatic step. In optimizing in this mode the cost of energy and equipment tends to decrease the severity of the pretreatment and increase the amount of required enzymes slightly.

In both cases, as the cost of enzymes is reduced, the severity of the pretreatment will most likely decline, while the reliance on enzymes will increase. In this manner, the process can be adapted to changing economics.

The whole stillage may also be concentrated prior to further processing. One way of concentrating the fiber in the whole stillage is to employ a separation step prior to pretreatment and fermentation. This would entail processing a portion of the whole stillage through a machine such as press or a centrifuge to separate the supernatant (thin stillage) and the solids portion (wet distiller's grains) then reintroduce the wet distiller's grains into the unprocessed portion of the whole stillage. This has the tendency to reduce the volume of liquid thereby reducing chemical and energy costs, as well as reducing the required fermentation volume. The vast majority of the fiber is contained in the solids within the wet distiller's grain and therefore the final product yield is virtually unchanged. The thin stillage from this process would either be used as recycle in the facility 10, or evaporated to form syrup. This syrup could either be sold separately, or dried in with the DDGS from the whole stillage fermentation process.

The whole stillage is then subjected to a pre-treatment process as depicted in block 204 of FIG. 2. In one embodiment, the pre-treatment process may be implemented with the equipment 50 generally illustrated in FIG. 3 and shown in more detail in FIG. 4. Referring to FIG. 4, the whole stillage is first transferred to a surge tank 52 or other vessel. Sulfuric acid or another acid is then added to the surge tank 52 to decrease the pH level of the whole stillage to promote dilute acid hydrolysis. Sufficient acid is supplied to decrease the pH of the whole stillage to 1.0 to 4.5 and preferably to 1.8. Some evidence suggests that lower pH values aid in oil recovery. The acid may alternatively be added in the main ethanol production facility before the whole stillage is diverted.

The pre-treatment portion of the process 200 continues by heating and pressurizing the whole stillage mixture. The optimum temperature of the mixture depends on a variety of factors including upstream treatments and retention times, downstream retention times, the mixture's pH value, and the enzyme treatments described herein. In one embodiment, the heating is performed in a hydro-heater 54 shown in FIG. 4 where high pressure steam is injected into the mixture to increase its temperature to 215° F. to 260° F., with the best results at 260° F. Higher temperatures up to 300° F. may be even more beneficial, but temperatures above 260° F. may be difficult to achieve economically. Heating by steam injection is beneficial because it results in cavitation of the mixture which further disrupts the structure of the fiber in the whole stillage which aids in subsequent processing of the whole stillage. Additional steam injection steps can be added to further break down the fiber. The number of steam injection steps is a trade-off between energy use and yield and product quality.

During the heating process, the whole stillage is also pressurized in the hydro-heater 54, a cook tube 56, or other vessel to a pressure in excess of the vapor pressure to prevent the mixture from boiling. The heated mixture is then held at the elevated temperature and pressure for 2-20 minutes. Applicant has discovered that retention times beyond 20 minutes don't provide substantial additional benefits, but are relatively inexpensive to implement. Increased residence times cost more up front, but the cost to operate with longer residence time is virtually identical to the process using shorter residence time. Therefore it can be economically attractive to implement the process with hydrolyzation in the pretreatment phase, which can be used to implement less severe conditions in other parts of the process, while retaining the same amount of fiber conversion. But increased retention times increase the production of other unwanted products, such as furfurals. This can lead to decreased fermentation performance.

Another method of heating the whole stillage is to use a heat exchanger where the steam, or other heating medium, does not come in contact with the whole stillage. This heating method produces very similar results to steam injection, but seems to require more residence time and is difficult to perform without fouling of the heat exchanger. This heating method also does not result in any cavitation of the whole stillage. Yet another method of heating the whole stillage uses a batch cooker.

The pre-treatment portion of the process 200 continues by transferring the whole stillage mixture to a flash tank 58 where its pressure is rapidly dropped, causing the mixture to boil and flash off steam. This rapid boiling causes further rupturing of the fiber structure of the whole stillage to further expose the cellulose and hemicellulose of the whole stillage. The flashing may be performed in one or more steps in one or more tasks. The steam from the flash tank 58 may be captured in a flash condensor 60 and used as make-up water in the slurry tanks or elsewhere in the ethanol production facility 10 as depicted in FIG. 4. Other methods may be used to create the cavitation, including pipe restrictions and/or using shearing pumps, or liquid mills.

Afterward, the whole stillage is cooled in one or more heat exchangers 62 to a temperature appropriate for the subsequent enzymatic hydrolysis process. Pentose sugars, such as xylose, may be produced from the hemicellulose by this portion of the method. Generally 70 to 100% of the final hemicellulose breakdown is achieved during the pre-treatment portion of the process 200 process. The importance of the enzymatic hydrolysis step described below depends on the severity of the pretreatment process. The less severe the pretreatment process, the more important the enzymatic hydrolysis is. The enzymatic process that follows releases a bit more sugars from the hemicellulose.

Hemicellulose has a tendency to hydrolyze to monomeric sugars quite effectively during the pretreatment. Since hemicellulose composition varies from one source to the next, hemicellulases are somewhat generic in their action patterns and as of this writing are not optimized for specific grain seed fibers. As hemicellulases are optimized, the yield of monomeric sugars from hemicellulose will tend to increase during enzymatic hydrolyzation. Currently, 70 to 100% of hemicellulose hydrolyzation occurs during the pretreatment, and the enzymatic portion accounts for only 0 to 30%. As hemicellulases are optimized, this ratio is expected to switch to 0 to 30% during pretreatment and 70 to 100% during enzymatic hydrolysis.

If no fermentation of hemicellulose is being conducted then the hydrolyzation is not required for fermentation. But the quality of the feed products, the ability to dry the feed, the viscosity of the stillage, and yield of oil can be greatly influenced by the hydrolyzation of the hemicellulose. The hemicellulose tends to bind liquids, especially water. The held water increases viscosity thereby increasing pumping requirements, and can increase the energy required to dry the final feed product. Oil can also become bound with the hemicellulose, which decreases oil yields. In addition, hemicellulose may be more digestable by monogastrics when hydrolyzed.

The mixture is then subjected to an enzymatic hydrolysis process as depicted in block 212 of FIG. 2. In one embodiment, the enzymatic hydrolysis process may be implemented with the equipment 64 shown generally in FIG. 3 and shown in more detail in FIG. 4. The enzymatic hydrolysis primarily converts the cellulose portions of the fiber to usable sugars but also converts some of the hemicellulose to sugars. The whole stillage is first transferred to one or more tanks 66 shown in FIG. 4 where enzymes are added. Ammonia or other chemicals may also be added to increase the pH to a level conducive to the activity of the enzymes. The specific or optimum conditions in the enzymatic hydrolysis process depend upon the enzyme used. In one embodiment, the whole stillage is held at a temp of 150° F.-160° F., with a preferred temp of 158° F. and a pH level of approximately 4.5. The whole stillage is then cooled in one or more heat exchangers 68 and, if necessary, pH corrected to a level of 4.8 to avoid denaturing the enzymes. Hexose sugars, such as glucose, may be produced from the cellulose by the enzymatic hydrolysis.

Depending on the nature of the enzyme used, the enzymatic hydrolysis can either be carried out during the fermentation steps described below where the temperature is held at a point that is conducive to fermentation, or as a separate step as described above in a separate tank where the temperature is held higher so the activity level of the enzymes is greater. The choice of a separate step or a simultaneous enzymatic and fermentation step depends on the activity of the enzymes used and on viscosity requirements. The whole stillage can become very viscous during the pretreatment steps, especially when cooled to fermentation temperature. It may therefore be necessary to cool the whole stillage to an intermediate temperature where the viscosity is lower and then add enzymes to breakdown the mixture further. The whole stillage can then be cooled to fermentation temperatures without excessive viscosity issues.

Different enzymes may be used to hydrolyze the hemicellulose and cellulose portions of the fiber. Hemicellulose composition varies from one fiber source to another, but all contain a variety of sugars with xylose generally being the most abundant. In corn fiber, xylose and arabinose are present in the highest concentrations. Mannose, glucose and other sugars are also present, but to a much smaller degree.

Hemicellulose can be broken down with enzymes that are currently commercially available, and by combining appropriate chemical and physical pretreatment methods the hydrolysis is quite effective. The enzymes used to hydrolyze hemicellulose are somewhat generically termed "hemicellulases." Hemicellulases contain several different enzymes that hydrolyze specific bonds in hemicellulose, but due to the fact that hemicellulose contains varying amounts of each of the sugars, varying amounts of each of the activities is required for an optimized hydrolyzation of all of the components. Hemicellulases are generally most effective at temperatures in the range of 155° F. to 185° F., with reduced activity at fermentation temperatures of 90° F. to 95° F. Since hemicellulose composition varies by feedstock, a hemicellulose which is most effective for the particular feedstock must be selected.

Cellulose is more difficult to convert to sugars because of it crystalline structure. The glucose is linked to form chains, with cross linking between the chains. This cross linking of the chains creates much of the difficulty in hydrolyzing cellulose; in effect it creates a crystal structure with a relatively small surface area to volume ratio. The most effective way of hydrolyzing cellulose is to pretreat it as described above to rupture the fiber structure thereby creating more surface area. The cellulases are then introduced to continue the breakdown of the cellulose to glucose.

The purpose of pretreating the cellulose is to increase susceptibility to enzymatic hydrolysis. Non-pretreated cellulose has a structure with a very small surface area to volume ratio. This limits the number of areas available for enzymes to attach and liberate glucose from the structure. This determines the effective upper limit for cellulase dosing, thereby limiting the hydrolysis rate. By pretreating the fiber, the crystalline structure is disrupted and more areas for attack are created. The hydrolysis rate is increased by decreasing polymerization of the cellulose and can be further increased by increased cellulase dosing.

Hydrolysis rates determine the required fermentation time. By increasing the rate of hydrolysis, the required fermentation time is reduced. This can be attractive if a fermentation organism capable of metabolizing the sugar as quickly as it is liberated is being used. The reduced fermentation time reduces the fermentation capacity required, thereby reducing capital costs.

The enzymatic hydrolysis of the pretreated cellulose is usually accomplished in three steps. The first step is to cleave long chains of glucose from the cellulose using a whole cellulase, which randomly hydrolyzes links in the cellulose. Since this action is random in its attack it can create anything from a single glucose unit to a chain that is few thousand glucose units long. This is generally the cheapest portion of a cellulase formulation, but since it is random it does not produce free glucose units at a reliable rate. It does however create more chains for the next enzymes to act upon.

The second step is carried out by cellobiohydrolase. This enzyme hydrolyzes two units of glucose, termed cellobiose, from the end of a cellulose chain. Since this is not a random attack the rate of production of cellobiose is reliable.

The third enzyme used is beta-glucosidase. This enzyme acts on the end of a cellulose chain to hydrolyze single units of glucose. The chain can be of any length from two units to thousands of units long.

The best way to cost effectively hydrolyze cellulose is to balance the use of each one of these enzymes. For the cellobiohydrolase and beta-glucosidase to be effective they need ends to work on. The production of more ends is the job of the whole cellulase.

To further complicate matters, the temperature optimum for each of these enzymes is slightly different. The whole cellulase generally operates best at temperatures from 150° F. to 185° F., while beta-glucosidase operates in temperatures below 130° F., and is denatured at the optimum temperatures of the whole cellulase.

In light of this, it can be most cost effective to perform the above described pretreatment steps at a temperature near 160° F. and the add the cellulase alone in the enzymatic hydrolysis step. This can reduce the viscosity of the fluid and provide more ends for the cellobiohydrolase and beta-glucosidase to work on in fermentation. This step can also utilize the whole cellulase working in tandem with the xylanase, which is usually a higher temperature enzyme.

If viscosity is not an issue, it can be more cost effective to perform all of the enzymatic hydrolysis in fermentation rather than in a separate step. This provides a less capital intensive up-front investment. Additionally, many of the most cost effective enzymes available today contain all three of these enzyme activities in one mixture. Currently the decision on using an enzymatic pretreatment is solely based on viscosity.

The severity of the pretreatment is mainly related to three parameters. The three parameters are temperature, pH and residence time. Overall temperature and pH have a much greater effect than residence time. Residence time has the greater affect on hemicellulose hydrolyzation.

Increased temperature, increased residence time, and reduced pH increase the severity of the pretreatment. Each of these parameters has to be balanced to optimize the process for different whole stillage and end goals. Increased temperature increases the energy usage of the process, and after a certain point can being to quickly degrade the sugars. This threshold appears to be at about 300° F. Decreased pH requires more acid, which increases chemical costs. Depending on the acid used, it can have negative effects on the value of the feed. Increased residence time increases up front capital costs, due to larger tank volumes, and can cause sugar degradation after prolonged periods.

To balance the pretreatment parameters, all products must be considered. For example, if the temperature were lowered in an attempt to reduce energy costs, more acid would be required. If sulfuric acid is used, the amount of sulfur in the feed can be increased to levels that can reduce the value of the feed. To prevent this, the treatment of the material within the starch to ethanol plant and the desired product yields and composition must be known and adjusted for during the optimization.

Lab Material Balance of a Representative Fermentation

| Sample id | Crude Protein | Crude Fat | Crude Fiber | Neutral Detergent Fiber | Acid Detergent Fiber | Phosphorus (total) | Ash |
|---|---|---|---|---|---|---|---|
| STD DDGS | 29.5 | 10.5 | 6.8 | 23.1 | 9.4 | 0.9 | 4.7 |
| Cell DDGS | 47.6 | 6.4 | 5.6 | 13.7 | 9.8 | 1.1 | 5.6 |

Lab Results from Feed Testing.

The line labeled STD DDGS is the current DDGS make up. The line labeled Cell DDGS is the DDGS after the residual starches and cellulose has been fermented, no hemicellulose was fermented in this test.

Cellulose Mass Balance

The cellulose content can be calculated by subtracting the ADF content from the NDF content. Therefore, the starting cellulose content was 13.7% of the dry matter. There were 93.5 grams of dry matter at the start, so there were 12.81 grams of cellulose before fermentation.

After fermentation the cellulose concentration was 3.9% and there were 88.0 grams of dry matter. This shows 3.26 grams of cellulose at the end. Dividing 3.26 grams by 12.81 grams shows that 25.4% of the cellulose was left, or that 74.6% of the cellulose had been removed.

Hemicellulose Mass Balance

ADF content is the concentration of hemicellulose and lignin. We have not yet measured the ratio of lignin to hemicellulose, but since we are not yet fermenting the hemicellulose it is inconsequential at this point. But by looking at the mass balance of the ADF we show that there was 8.79 grams of ADF at the start of fermentation, and 8.62 grams at the end. This small amount was most likely consumed by bacteria during the fermentation.

Starch Mass Balance

Total starch concentrations dropped from 4.5% to 0.3% during fermentation. Calculations show 4.21 grams of starch initially, and 0.28 grams at the end of fermentation. 93% of the starch was used during fermentation.

Fermentation Discussion

During the first 4 to 6 hours of the fermentation little to no ethanol is produced. It is during this phase that the yeast are reproducing. The starch is the most accessible sugar during these early stages, therefore the production of the yeast cells is fueled by mainly by the starch. During the post reproduction phase of fermentation the yeast begin to produce ethanol. This occurs as glucose is slowly liberated from the cellulose chains. It is therefore assumed that the while the starch component produces yeast, the cellulose component produces ethanol.

From the above calculations 3.93 grams of starch were used in the fermentation and 9.55 grams of cellulose were used. The relative percentages of sugars used in fermentation were 29% starch and 71% cellulose. During this fermentation 5.87 grams of ethanol were produced. Theoretical yields of ethanol would show that 11.48 grams of sugar would be required to produce this much ethanol. This leaves 2.00 grams of sugar, which are assumed to be used for yeast production.

The whole stillage is next fermented as depicted by block 208 in FIG. 2 and equipment 70 in FIG. 3. The fermentation of the mixed sugars produced in the pre-treatment and enzymatic hydrolysis steps described above requires an organism different than the yeast used in the fermentation step of the main ethanol production facility 10. *Saccharomyces cerevisiae* is only able to ferment hexose sugars, and therefore cannot use the pentose sugars unlocked from the hemicelluloses. Another yeast or bacteria is needed to perform this step.

*Saccharomyces cerevisiae* can be used, but two outcomes occur. Either an infectious organism begins to consume the pentose and some of the hexose sugars, or no infection occurs and the pentose sugars remain in solution. In the first case, the final acid detergent fiber content of the whole stillage byproduct of the process 200 is reduced and protein content is increased, with a slight change in amino acid profile. In the second case, the acid detergent fiber levels of the whole stillage byproduct remain higher with a resultant reduction in the percentage of protein.

The two front runners for the mixed sugar fermentation are both yeasts. The two strains are very similar in most respects. The first strain, *Pichia Stipitis*, is the most likely candidate because it is readily available. *Candida Shehatae* is the second candidate, but it is similar in most respects to *Pichia Stipitis* except that it is less readily available.

These yeasts are able to ferment both the glucose and the xylose contained in the mixture. This is a trait which greatly enhances the process 200. Fermentation times appear rather long, with 70 to 100 hours as the range found in other publications. The upper final ethanol concentrations these yeasts can survive is around 3.5 to 5 wt %. This is not an issue as the whole stillage is dilute enough to only produce final ethanol concentrations of around 1.5 to 3 wt %. If either of these yeasts are used, the entire fermentation would be carried out by the *Pichia Stipitis* or *Candida Shehatae*. No co-fermentation with *Saccharomyces cerevisiae* would be required, but could be done.

The fermentation step of the process 200 enhances the nutrient value of the final byproduct of the process 200. The yeasts are rich in proteins and are used to enhance the protein levels and the amino acid profiles of the whole stillage byproduct of the process 200. It would therefore be conceivable that someone could want to produce only yeast during this process, without the production of additional ethanol. This could remove the requirement for the distillation 72 and enhance the feed produced from the whole stillage byproduct even further.

A total fermentation time of ~20 hours can be used to ferment ~80% of the available sugars. This gives reasonable results to the process 200. However, additional time allows more fiber to be hydrolyzed and fermented, improving yields and feed composition. Generally, by 90 to 100 hours, the fermentation is nearly halted due to exhaustion of the feedstock. If fermentation is further extended beyond this point, the yeast will go through autolysis and begin to consume their own structural carbohydrates. This step increases the protein levels of the whole stillage byproduct but does little to nothing for final ethanol yields.

After fermentation, whole stillage is distilled and separated as depicted by block 210 in FIG. 2 to remove ethanol from the whole stillage. The distillation may be performed in one or more distillation columns 72 depicted in FIG. 3. The distillation portion of the process 200 is similar to the distillation that occurs in the distillation columns 24 of the main ethanol production facility 10. The ethanol or alcohol exits the top of the columns 72 and is transferred to one or more rectifiers to remove moisture from the alcohol. The alcohol may also be passed to one or more molecular sieves to remove even more moisture. The final alcohol is then transferred to one or more ethanol holding tanks where it may be denatured before use as a fuel or fuel additive. The alcohol from the distillation columns 72 may be transferred to the rectifiers 26 and sieves 28 of the main ethanol production facility 10 where it is comingled with the ethanol from the distillation columns 24 or it may be purified by its own dedicated rectifiers and sieves.

The whole stillage that remains in the distillation columns 72 after the alcohol has been removed falls to the bottom of the distillation columns and is then transferred to one or more whole stillage holding tanks 74. The whole stillage at this point is similar to the whole stillage obtained at the beginning of the process 200 except that it has less solids and higher protein. The whole stillage may then be passed through one or more centrifuges 76 which separate the whole stillage into a stream of thin stillage and a stream of wet distillers grain. The thin stillage may be held in one or more tanks 78 and is typically returned to the slurry tanks 18 or some other part of the ethanol production facility 10 that requires water. Some or all of the thin stillage may also be transferred to one or more evaporators 80 to produce evaporated thin stillage, which is commonly referred to as "syrup". The syrup may be held in one or more tanks 82 and be used as an animal feed additive.

The wet distillers grain, which is often referred to as "wet-cake", may be held in storage facilities 84, 86 and also sold as a livestock feed. Some of the wet distillers grain may be passed through one or more dryers 88 to remove liquid therefrom to produce dried distillers grain, which may be stored in one or more tanks 90 and used as dry livestock feed. The syrup from the tanks 82 may also be dehydrated in the dryers 88 forming dried distillers grain with solubles (DDGS).

The process 200 and systems described above provide numerous benefits. For example, the process 200 recovers additional ethanol from the whole stillage byproduct of the primary ethanol production facility 10, thus increasing the ethanol yield of the facility. Moreover, the process 200 also improves the quality of the final whole stillage byproducts. The dried distillers grain produced by the main ethanol production facility 10 has a high fiber content that is difficult for monogastrics to digest. The process 200 of the present invention uses that fiber as a carbohydrate that is metabolized by the fermentation step. During the initial stages of fermentation, the added yeast goes through a growth phase where the carbohydrates and available nitrogen are used to produce more yeast cells. The yeast are high in protein content and also produce essential amino acids. The reduction of fiber and increase of protein content produces a feed that is more digestable for monogastrics, and therefore much higher in value.

A conventional corn to ethanol process produces the following from one bushel of corn:

| Product | Yield | |
|---------|-------|---|
| Ethanol | 2.75 | Gallons per Bushel |
| DDGS | 16.4 | Pounds per Bushel |
| Corn Oil | 0.45 | Pounds per Bushel |

In contrast, an embodiment of the process 200 of the present invention produces the following from one bushel of corn:

| Product | Yield | |
|---------|-------|---|
| Ethanol | 3.02 | Gallons per Bushel |
| DDGS | 11.3 | Pounds per Bushel |
| Corn Oil | 1.5 | Pounds per Bushel |

Moreover, the process 200 improves the nutrient content of the final DDGS byproduct as follows:

| Type | Protein | Fat | Crude Fiber |
|------|---------|-----|-------------|
| Prior Art | 30% | 10% | 7% |
| Process 200 | 50% | 3% | 2% |

Embodiments of the invention may also be used to ferment whole stillage to other products. The sugars produced through the process 200 are relatively low in concentration as compared to traditional starch fermentations. This low concentration of fermentable sugars translates into low final concentrations of products. This allows fermentations with products that are toxic to the fermentation organism to be carried with low residual sugars.

One example of such a fermentation would be acetone, butanol, ethanol (ABE) fermentation. In this fermentation, butanol is toxic to the host organism at concentrations around 2%. If whole stillage is not concentrated prior to the fermentation, sugar concentrations of 3 to 4 wt % are expected. This would translate to final butanol concentrations of less than 2%. While ABE fermentation is used as the example many other types of fermentations would be well suited to this process.

The process 200 also improves corn oil recovery by breaking down and fermenting the fiber in the fat rich germ portion of the kernel. In prior art processes, the oil tends to become trapped within the fiber matrix of the germ, making it difficult to remove. Most reports of oil recovery in corn to ethanol plants with oil removal report yields of 15 to 35% of the total oil. By breaking down the fiber this number can increase to nearly 100% of total oil.

Although the invention has been described with reference to the embodiments illustrated in the attached drawing figures, it is noted that equivalents may be employed and substitutions made herein. For example, the particular equipment shown in FIGS. 1, 3 and 4 may be replaced with other equipment without departing from the scope of the invention as recited in the claims.

Having thus described the preferred embodiment of the invention, what is claimed as new and desired to be protected by Letters Patent includes the following:

1. A process of producing ethanol from whole stillage, the method comprising:
   obtaining a supply of whole stillage from an ethanol production facility;
   pre-treating the whole stillage to convert hemicellulose portions of the whole stillage into sugars, the pre-treating step comprising:
      adding acid to the whole stillage to decrease its pH level;
      heating and pressurizing the whole stillage in a hydro-heater where steam is injected to cause cavitation of the whole stillage;
      holding the whole stillage under pressure and heat for a dwell time;
      removing pressure from the whole stillage to cause flashing;
      capturing steam from the flashing in a flash condenser for reuse; and
      cooling the whole stillage;
   adding enzymes to the whole stillage to convert cellulose portions of the whole stillage into sugars;
   fermenting the whole stillage to create a beer mixture;
   distilling the beer mixture to separate ethanol therefrom; and
   transferring the ethanol from the distilling step to the ethanol production facility to be combined with ethanol produced by the ethanol production facility.

2. The process of claim 1, wherein the enzymes added include cellulase, cellobiohydrolase, and beta-glucosidase.

3. The process of claim 1, further comprising cooling the whole stillage to an intermediate temperature and then cooling the whole stillage to a fermenting temperature, wherein the enzymes are added to the whole stillage at the intermediate temperature.

4. The process of claim 1, further comprising using the captured steam in slurry tanks.

5. A process of producing ethanol from whole stillage, the method comprising:
   obtaining a supply of whole stillage from an ethanol production facility;
   pre-treating the whole stillage to convert hemicellulose portions of the whole stillage into sugars, the pre-treating step comprising:
      adding acid to the whole stillage to decrease its pH level;
      pressurizing the whole stillage and heating the whole stillage to a temperature of approximately 215 degrees Fahrenheit to approximately 260 degrees Fahrenheit;
      directing the whole stillage through at least one pipe restriction to cause cavitation of the whole stillage;
      holding the whole stillage under pressure and heat for a dwell time;
      removing pressure from the whole stillage to cause flashing; and
      cooling the whole stillage;
   adding enzymes to the whole stillage to convert cellulose portions of the whole stillage into sugars;
   fermenting the whole stillage to create a beer mixture;
   distilling the beer mixture to separate ethanol therefrom; and
   transferring the ethanol from the distilling step to the ethanol production facility to be combined with ethanol produced by the ethanol production facility.

6. The process of claim 5, further comprising cooling the whole stillage to an intermediate temperature and then cooling the whole stillage to a fermenting temperature, wherein the enzymes are added to the whole stillage at the intermediate temperature.

7. A process of producing ethanol from whole stillage, the method comprising:
   obtaining a supply of whole stillage from an ethanol production facility;
   pre-treating the whole stillage to convert hemicellulose portions of the whole stillage into sugars, the pre-treating step comprising:
      adding acid to the whole stillage to decrease its pH level;
      heating and pressurizing the whole stillage;
      holding the whole stillage under pressure and heat for a dwell time;
      removing pressure from the whole stillage to cause flashing; and
      cooling the whole stillage;
   adding whole cellulase to the whole stillage at a temperature of approximately 150 degrees Fahrenheit to approximately 185 degrees Fahrenheit to convert cellulose portions of the whole stillage into sugars;
   cooling the whole stillage to a fermenting temperature;
   adding cellobiohydrolase and beta-glucosidase to the cellulose at the fermenting temperature to produce cellobiose and glucose, respectively;
   fermenting the whole stillage to create a beer mixture;
   distilling the beer mixture to separate ethanol therefrom; and
   transferring the ethanol from the distilling step to the ethanol production facility to be combined with ethanol produced by the ethanol production facility.

8. The process of claim 7, further comprising directing the whole stillage through a shearing pump to cause cavitation of the whole stillage.

9. The process of claim 7, further comprising directing the whole stillage through a liquid mill to cause cavitation of the whole stillage.

10. The process of claim 7, further comprising directing the whole stillage through at least one pipe restriction to cause cavitation of the whole stillage.

* * * * *